United States Patent [19]

Dudasik et al.

[11] Patent Number: 5,607,431
[45] Date of Patent: Mar. 4, 1997

[54] PROSTHETIC HIP IMPLANTATION METHOD AND APPARATUS

[75] Inventors: Michael W. Dudasik, Nutley; Matthew P. Poggie, Union City; Michael J. Schulzki, Boonton, all of N.J.

[73] Assignee: Howmedica Inc., New York, N.Y.

[21] Appl. No.: 386,046

[22] Filed: Feb. 9, 1995

[51] Int. Cl.⁶ ................................................ A61B 17/56
[52] U.S. Cl. ................... 606/80; 606/86; 606/96; 606/99; 606/102
[58] Field of Search ................... 606/79, 80, 84, 606/85, 86, 87, 88, 89, 96, 97, 98, 99, 102, 104

[56] References Cited

U.S. PATENT DOCUMENTS

| | | | |
|---|---|---|---|
| 4,959,066 | 9/1990 | Dunn et al. | 606/87 |
| 5,007,936 | 4/1991 | Woolson | 623/23 |
| 5,089,004 | 2/1992 | Averill et al. | 606/85 |
| 5,108,405 | 4/1992 | Mikhail et al. | 606/80 |
| 5,122,134 | 6/1992 | Borzone et al. | 606/79 |
| 5,152,792 | 10/1992 | Watkins et al. | 606/87 |
| 5,192,283 | 3/1993 | Ling et al. | |
| 5,342,363 | 8/1994 | Richelsoph | 606/89 |
| 5,342,366 | 8/1994 | Whiteside et al. | 606/86 |
| 5,360,446 | 11/1994 | Kennedy | 623/16 |
| 5,464,406 | 11/1995 | Ritter et al. | 606/86 |

FOREIGN PATENT DOCUMENTS

| | | |
|---|---|---|
| 206777A | 12/1986 | European Pat. Off. |
| WO8801854A | 3/1988 | WIPO |
| WO9412124A | 6/1994 | WIPO |
| WO9514433A | 6/1995 | WIPO |

OTHER PUBLICATIONS

Joint Medical Products—S-Rom Tri-Version Surgical Technique.
HG Multilock Hip Pros.—Surgical Technique-William Harris.
Impact Modular Total Hip System-Dr. Whiteside.
Dow Corning Wright brochure-1985-Infinity.
Howmedica Sales Bulletin-Feb. 9, 1993.
Osteonics -Surgical Protoco-Omniflex Femoral System.
Whiteside Total Hip System brochure-1985.

*Primary Examiner*—Michael Powell Buiz
*Assistant Examiner*—Mark S. Leonardo
*Attorney, Agent, or Firm*—Peter C. Richardson; Lawrence C. Akers; Raymond W. Augustin

[57] ABSTRACT

A surgical instrument system for preparing the medullary canal of the femur for implanting a prosthetic femoral component includes a template to be used in determining osteotomy position from an x-ray. A gauge is provided to locate and mark this position on the anterior femur. A distal reamer having an elongated drive shaft is used to form the canal to receive the distal stem of the femoral component. A metaphyseal template is used to determine the proper anteversion/retroversion and a chisel is used to cut the lateral area of the femur, both of which are guided by the elongated reamer shaft. A proximal broach also guided by the reamer shaft is used to shape the proximal medullary canal.

23 Claims, 12 Drawing Sheets

PROSTHETIC HIP IMPLANTATION METHOD AND APPARATUS

BACKGROUND OF THE INVENTION

1. Field of the Invention

The present invention relates to a method for implanting prosthetic implant devices and, more particularly, to a method for implantation of a femoral stem of a total hip system within the femoral canal of a femur.

2. Description of the Prior Art

The use of prosthetic implants to replace natural joints of the body, such as the hip, are well known. In hip joints, it is very often required to replace the head of the femur with a prosthetic head which requires the implantation of a prosthetic stem within the medullary canal of the femur. Heretofore the procedures for implanting a prosthetic stem include the use of a broach or rasp, usually as a last step in preparing the femoral canal for the reception of the prosthetic stem. The use of the broach or rasp as a last step is designed to provide an accurate and precise fit of the stem within the canal.

Such a broach or rasp system is shown in U.S. Pat. No. 5,089,004 dated Feb. 18, 1992 with an identical broach or rasp system shown in the 1985 Dow Corning Wright brochure entitled "The Whiteside Total Hip System".

While these instruments do provide for an accurate gauge of the shape of the broached cavity in the femur, they do not provide any means of accurately orienting the cavity itself. There has been shown a need for an instrument system which can reproduce the natural anatomy of the patient, as shown by his pre-operative x-rays, upon the implantation of a femoral component within the patient's femoral canal.

The present invention consists of a series of instruments and method for their use which accurately prepares the cavity for a precise fit with the stem and accurately orients the cavity within the medullary canal so that the patient's natural motion is duplicated upon replacement of a natural hip with a prosthetic hip. The instrument system includes a series of reamers and broaches and other instruments for locating the various bone removal operations to form a cavity precisely mimicking the stem to be implanted.

SUMMARY OF THE INVENTION

It is therefore an object of the invention to provide a series of instruments to be used in the implantation of a prosthetic femoral component.

It is a further object of the invention to provide a system of instruments and a method for their use which not only produces a cavity of the precise shape required, but precisely orients that cavity within the canal of the patient's femur.

These and other objects are achieved by a method in which a template corresponding to the prosthetic hip implant is placed on an x-ray of the femur to determine location of an osteotomy cut with respect to the sulcus of the femur. An osteotomy gauge is provided to transfer the templated dimension for the osteotomy cut to the femur. The gauge is located off the sulcus and is used to mark the precise location, preferably on the anterior surface of the femur. An osteotomy is then performed in a normal fashion. An osteotomy guide may be provided for this purpose.

After the osteotomy is performed, an awl is used to create a pilot hole through the proximal cancellous bone and into the medullary canal. The distal medullary canal is then prepared with a reamer mimicking the shape of the distal stem portion of the chosen femoral component. This shape is a generally conic or parabolic surface of revolution. The reamer has an elongated shaft extending proximally. The reaming depth is determined by a reamer depth gauge mounted either on the elongated shaft of the reamer or a cylindrical cutter on the reamer, which when aligned with the mark made with the osteotomy gauge on the anterior portion of the femur, sets the proper depth of the distal tip of the reamer and therefore implant.

A metaphyseal template is then placed on the elongated shaft which template mimics the proximal medial aspect of the hip stem to be implanted, thus aiding in sizing the femoral implant. This metaphyseal template may be rotated on the shaft of the reamer to thereby determine the proper anteversion/retroversion orientation of the hip stem. Upon determining the proper orientation, the template is anchored in place and a chisel having a shape of the lateral portion of the femoral implant at the osteotomy level is placed on an alignment element of the template and is used to remove the lateral portion of bone to form a shape corresponding to the lateral shape of the hip stem at the osteotomy level.

The chisel and medial template are then removed from the elongated shaft of the reamer and a broach having a shape mimicking but slightly undersized compared to the proximal portion of chosen implant stem is then placed over the shaft to, upon broaching, form the rough size of the proximal portion of the medullary canal cavity. The proximal broach and reamer may then be removed and a full-size broach corresponding to the actual implant is then placed in the cavity to finalize the preparation to the exact dimensions required and to serve as a receptacle for a trial prosthetic head and neck in the performance of a trial reduction of the joint to ensure that proper physiological locations within the hip joint have been achieved.

It can be seen that a kit of instruments is required with templates, reamers, gauges and broach components corresponding to each size of hip stem implant may be provided. Thus, once the proper size of hip stem implant is determined from the xray and stem template, the corresponding set of instruments would be chosen for the preparation of the canal to receive this chosen hip implant.

These and other objects and advantages of the present invention will become apparent from the following description of the accompanying drawings, which disclose several embodiments of the invention. It is to be understood that the drawings are to be used for the purposes of illustration only and not as a definition of the invention.

BRIEF DESCRIPTION OF THE DRAWINGS

In the drawings, wherein similar reference characters denote similar elements throughout the several views.

DESCRIPTION OF THE PREFERRED EMBODIMENT

Figure 1:
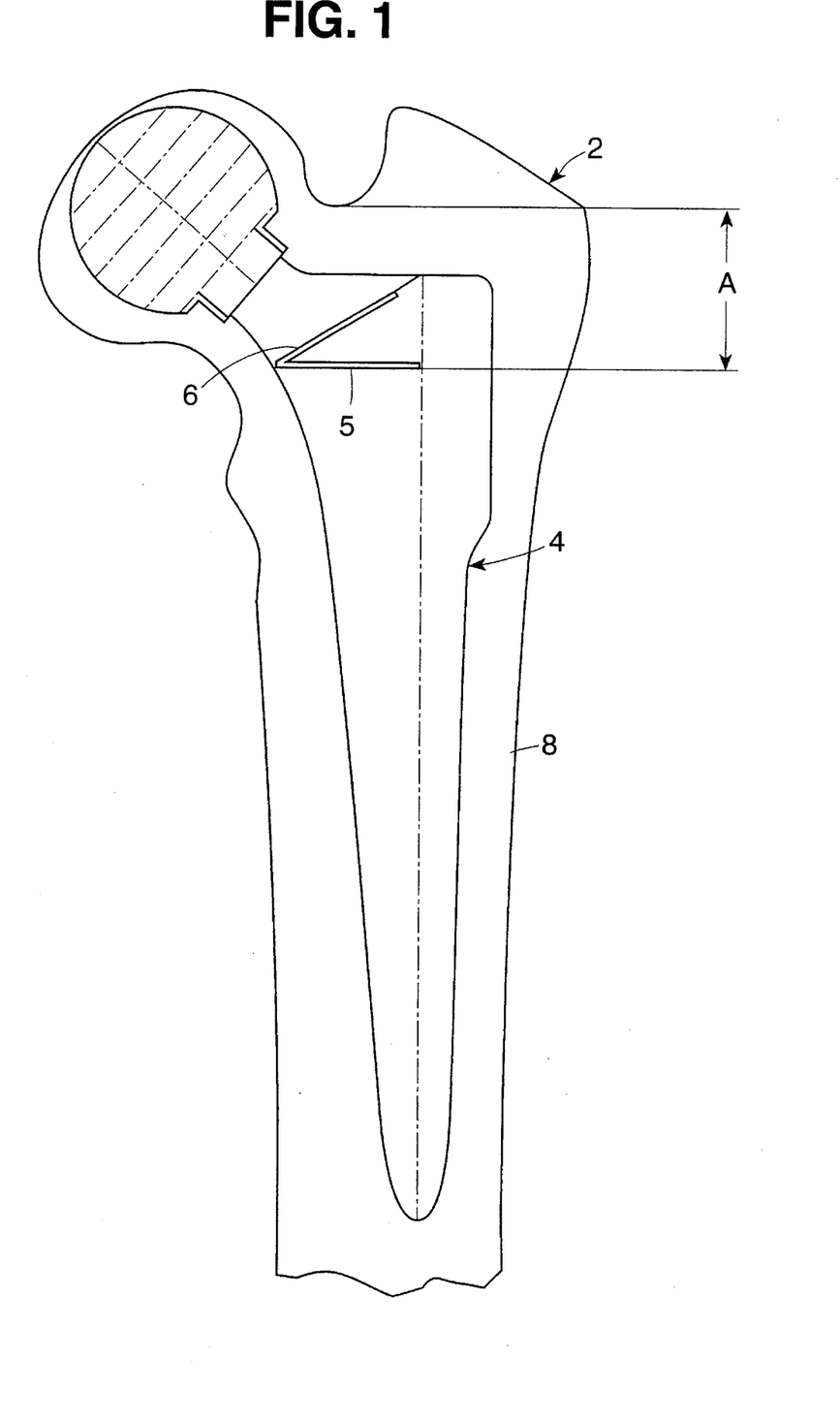
FIG. 1 shows a template of the prosthesis to be implanted placed over an x-ray of the patient's femur.

Referring to FIG. 1 there is shown an x-ray 2 of the femur 8 of a patient with an implant template 4 positioned thereon. Template 4 is an anterior view of the hip stem to be implanted. The template 4 includes a pair of slots 5 and 6, the function of which is to allow the surgeon to mark x-ray 2 to locate a marking device described below.

Figure 1A:
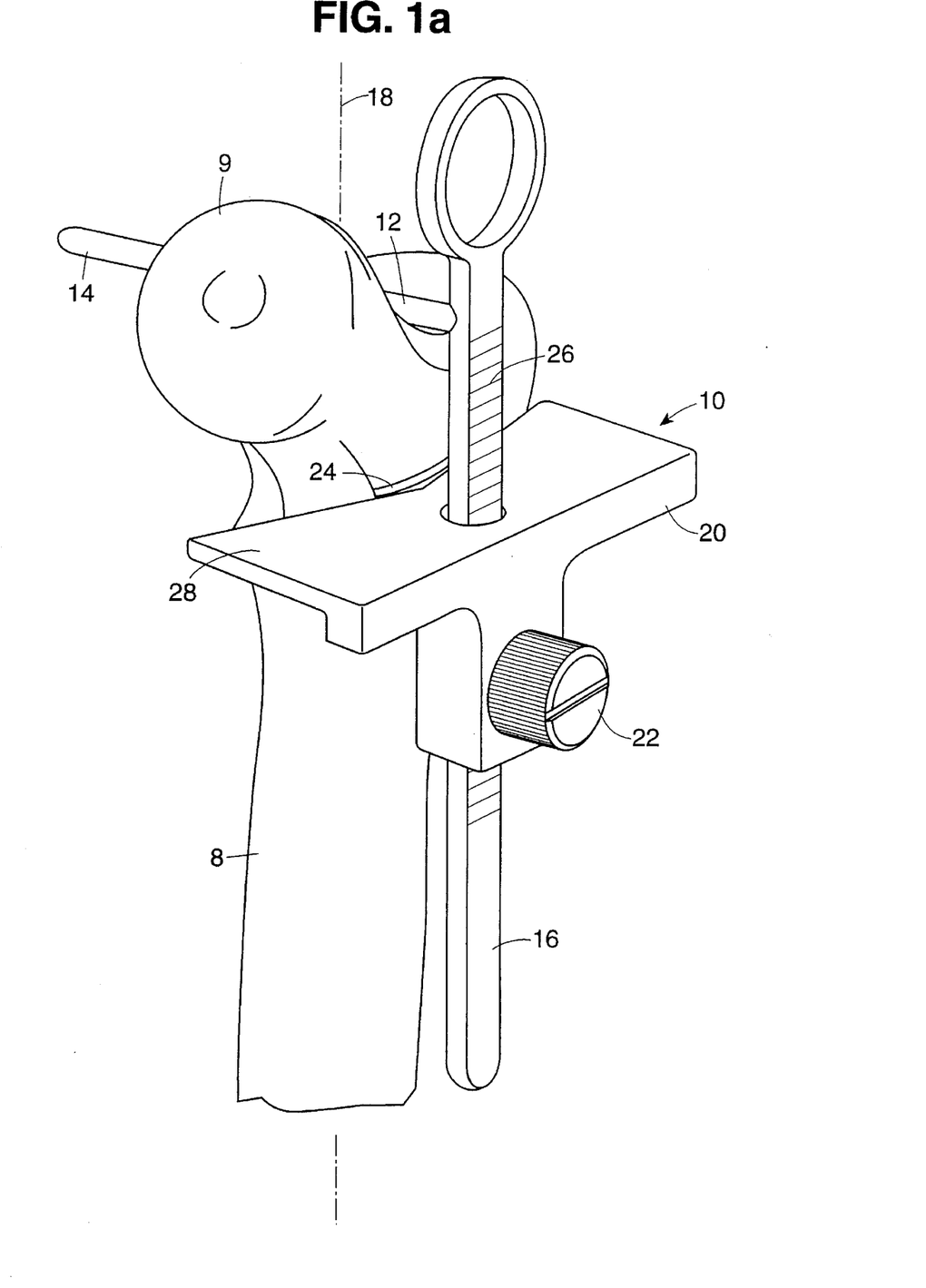
FIG. 1a is an isometric view of the femur with osteotomy height gauge of the present invention mounted thereon.

Referring to FIGS. 1 and 1a there is shown femur 8 including a head 9 with an osteotomy height gauge generally denoted as 10 placed thereon. Gauge 10 a posteriorly extending rod or arm 14 to be placed on the sulcus 12 of femur 8. Rod 14 is integral with and at right angles to a graduated guide shaft 16 and aligns the guide shaft 16 parallel to the long axis 18 of the femur 8. Gauge 10 includes a marking platform 20 which is slidably mounted on guide shaft 16 for movement in the proximal distal direction with respect to axis 18. Set screw 22 locks platform 20 in the proximaldistal direction on guide shaft 16 at a location 24 corresponding to slot 5 as determined from the x-rays.

Location 24 is determined preoperatively through the x-ray templating of the affected joint described above and serves as a reference for proximal-distal location of the osteotomy, ie., the location of the cut made by the surgeon to remove the femoral head. To determine location 24, the distance "A" between the underside of rod 14, ie., the surface of sulcus 12 is measured on an x-ray of the patient's femur to a reference point on a template of the hip stem to be implanted. This measured distance is then transferred to the height gauge 10 via calibrations 26 on guide shaft 16 and a reference mark placed at location 24.

In the preferred embodiment the calibrations 26 are approximately every millimeter so that the xoray template measurement may be accurately transferred. Preferably, this is done prior to placing the gauge 10 on femur 8. After the gauge 10 is placed on femur 8, location 24 is marked on the anterior or posterior surface of the proximal femur. Note that FIG. 1 shows the marking at location 24 on an anterior surface of the femur. The upper surface 28 of platform 20 is used to guide a marking device such as a cautery, a shallow saw cut or even a bio-compatible dye to mark the bone. Once location 24 is marked in some manner, gauge 10 is removed.

Figure 2:
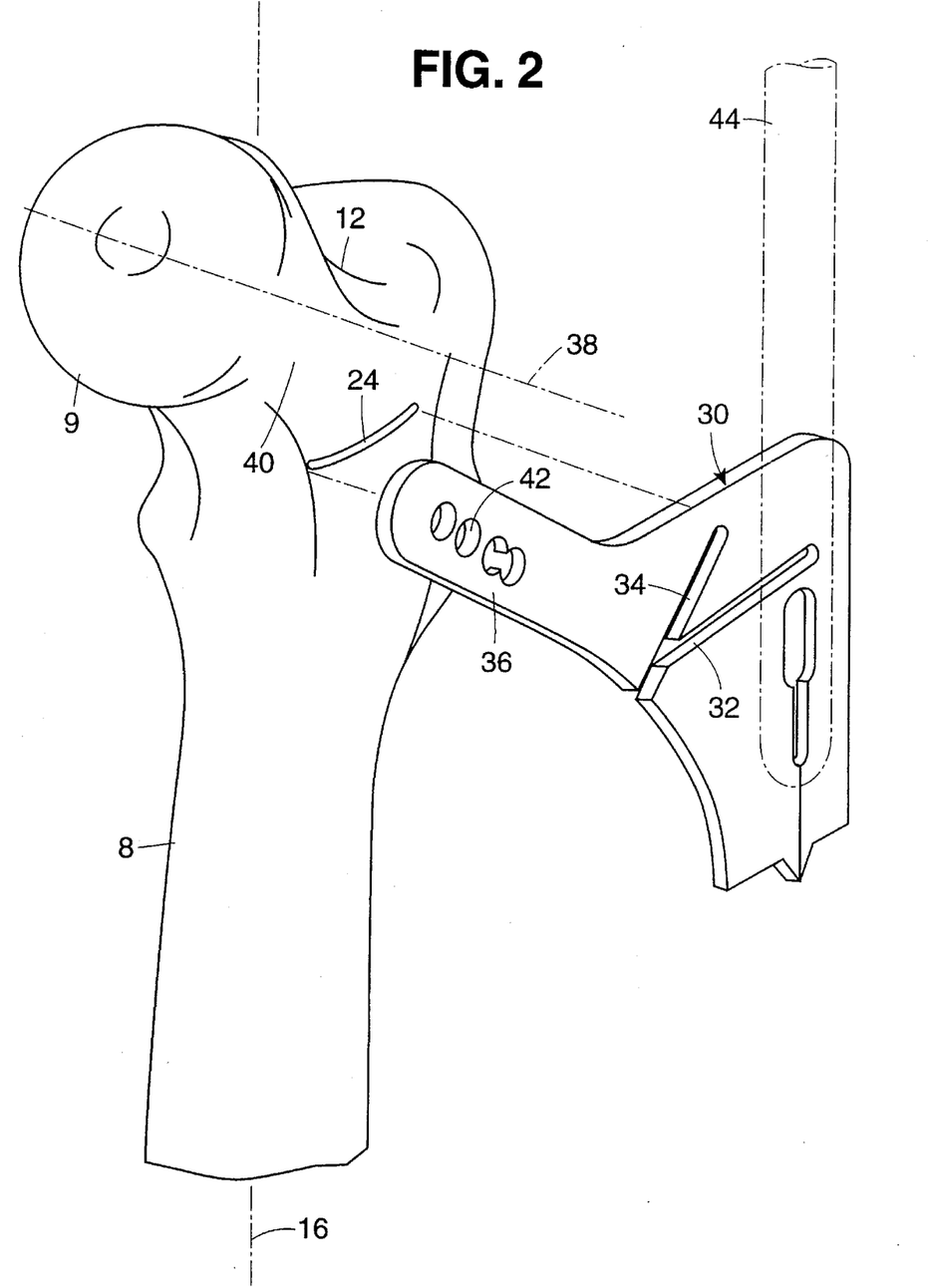
FIG. 2 is an isometric view of the femur with the osteotomy guide of the present invention shown in a position prior to contact with the anterior surface of the femur.
Figure 3:
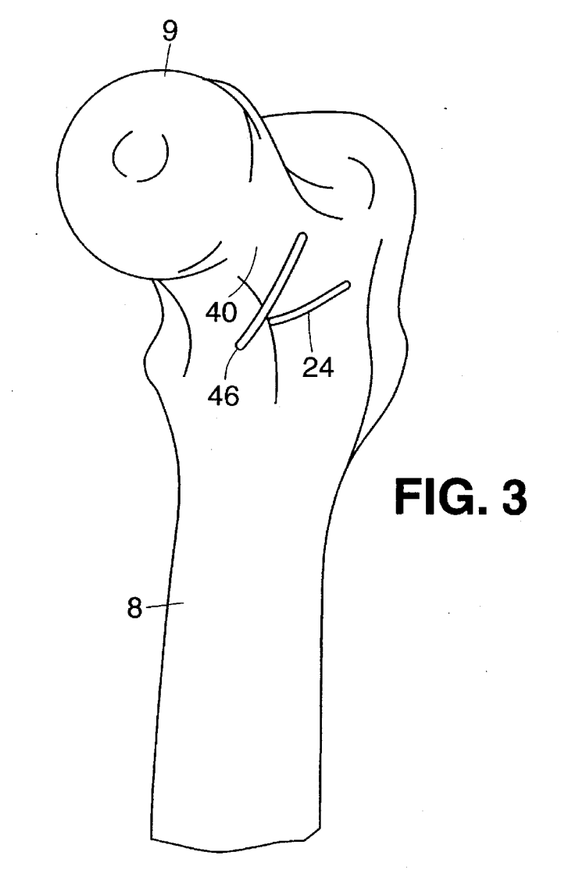
FIG. 3 is an isometric view of the femur showing the marks used to locate the osteotomy determined by the height gauge and guide shown in FIGS. 1 and 2.

Referring to FIGS. 2 and 3 there is shown an osteotomy guide generally denoted as 30. Guide 30 is in the form of a plate having a medial to lateral oriented slot 32 which corresponds to reference mark 24 placed on the femur 8. Guide 30 has a slot 34 denoting the preferred location of the osteotomy level. Guide 30 also has a portion 36 extending generally parallel to the axis 38 of neck 40 of femur 8.

Portion 36 includes a series of holes 42 to show the location of the prosthetic head after the osteotomy and implantation of the chosen prosthetic hip stem. To facilitate use of guide 30, a handle 44 is mounted, preferably in a removable fashion, to guide 30. Handle 44 may also be used to maintain the alignment of guide 30 with respect to the long axis 18 of the femur.

Slot 32 is aligned with the mark made at location 24 and slot 34 is then used to mark the osteotomy location 46 on the same surface of the femur as location 24 was marked, ie., in this case the anterior surface. This location is shown on FIG. 3. The guide 30 is removed and the osteotomy performed freehand. Alternatively, slot 34 may be used to guide a saw blade (not shown) to perform the entire osteotomy. In any event, after the osteotomy is performed using a saw, the result is shown in FIG. 4.

Figure 4:
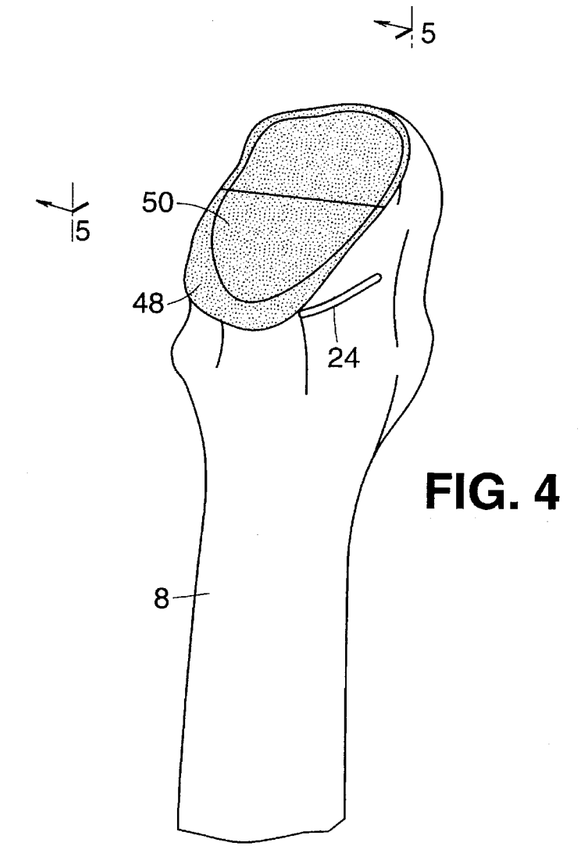
FIG. 4 is an isometric view of the femur after the osteotomy has been performed.
Figure 5:
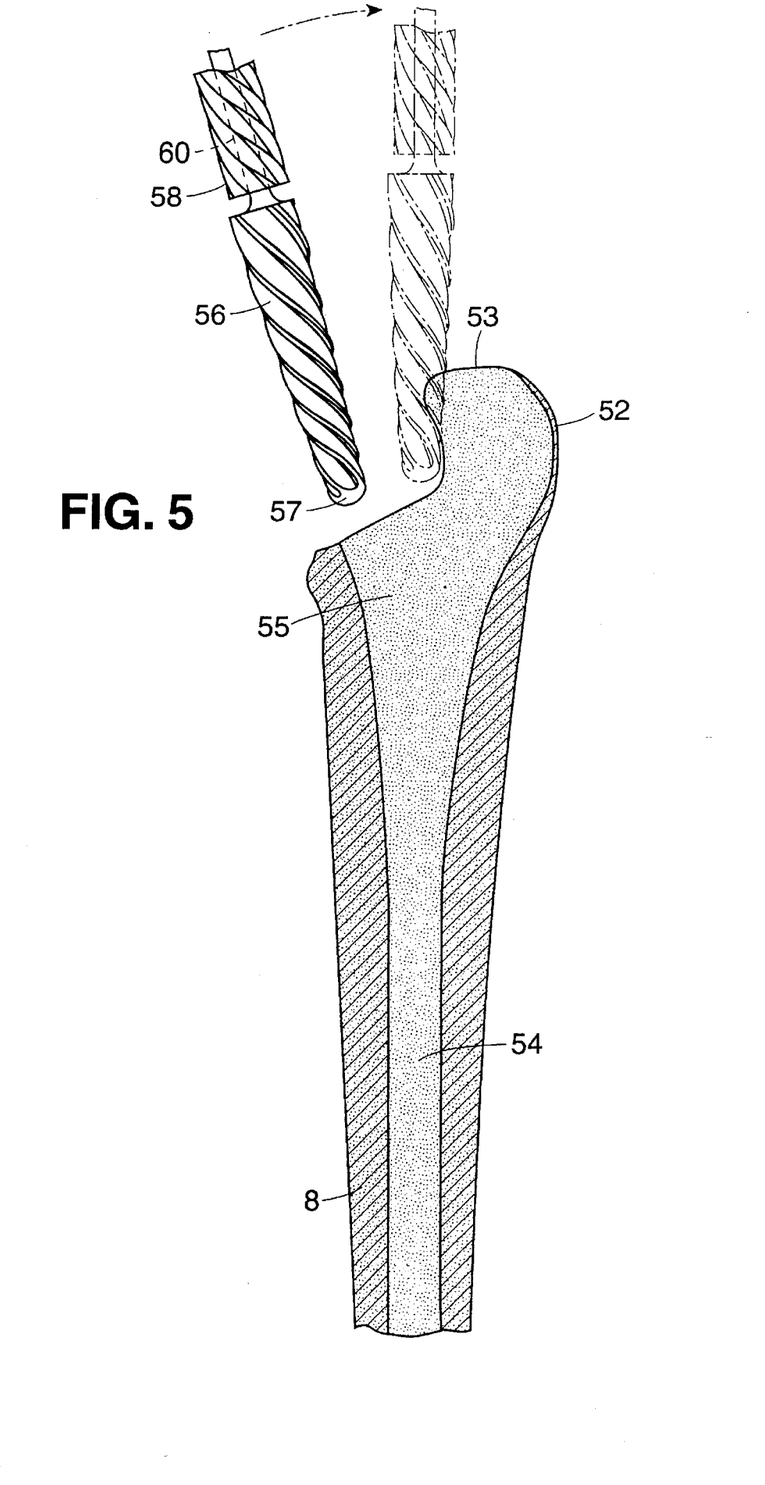
FIG. 5 is a side view of the reamer and trochanteric burr of the present invention with the femur shown in cross-section along lines 5—5 of FIG. 4.

FIG. 4 shows the resected proximal femur after the osteotomy. The cortical bone portion of the femur is denoted as 48 and the cancellous bone portion is denoted as 50. Referring to FIG. 5 there is shown a coronal cross-sectional view of femur 8 along line 5—5 of FIG. 4 immediately after the osteotomy. Shown are greater trochanter 52, metaphysis 55 and medullary canal 54. Cancellous bone 50 is first pierced by an awl (not shown) to provide a pilot opening into medullary canal 54 in the area of the metaphysis 55 for the reamer 56.

Figure 6:
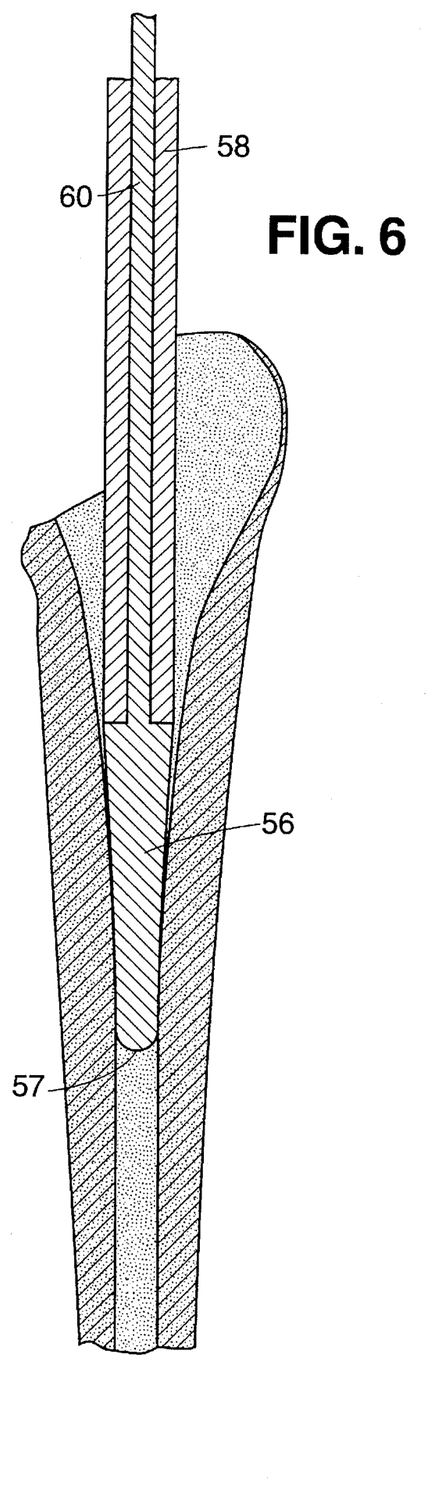
FIG. 6 is a cross-sectional view of the femur with the reamer and burr of the present invention in the medullary canal.
Figure 6A:
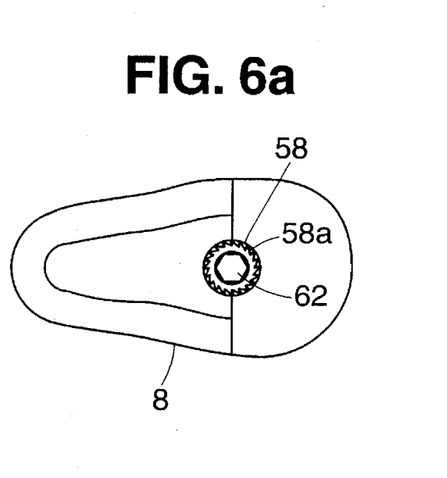
FIG. 6a is a top view of the femur, reamer and burr of FIG. 6.
Figure 7:
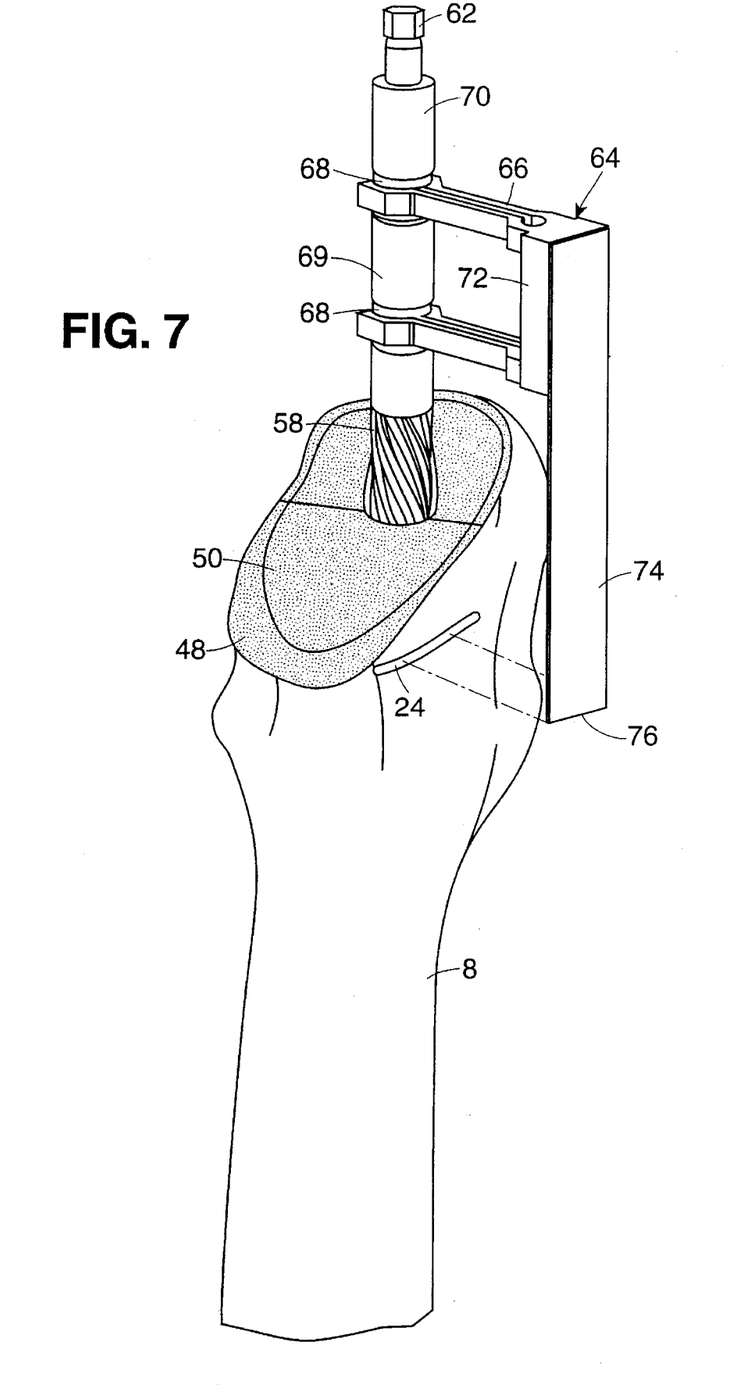
FIG. 7 is an isometric view of the femur with the reamer depth gauge of the present invention mounted on the reamer/burr combination of FIG. 6.

Referring to FIGS. 5 through 7 there is shown a helically fluted distal reamer 56 with a drive shaft 60 slidably received within helically fluted burr sleeve 58. In the preferred embodiment, reamer 56 including a drive shaft 60 is designed to be driven by a power tool (not shown). The drive shaft 60 includes a polygonal (preferably hexagonal) outer portion at least along part of its length, preferably at the head or top portion. In the preferred embodiment, burr sleeve 58 includes teeth 58a and a polygonal (preferably hexagonal) bore so that upon rotation of shaft 60, burr sleeve 58 is also driven. In the preferred embodiment, reamer 56 has a shape identical to the distal portion of the stem chosen for implantation. For example, a reamer and stem having a generally parabolic or conical surface of revolution may be used. Of course, a cylindrical surface is also acceptable.

Referring to FIG. 7 there is shown a reamer depth gauge generally denoted as 64. Depth gauge 64 is mounted on the proximal end of burr sleeve 58 in a manner which permits the sleeve 58 and reamer 56 to rotate while depth gauge 64 remains stationary.

In the preferred embodiment, the mounting arrangement includes a pair of arms 66 which snap onto a pair of grooves 68 formed in a smooth portion 69 of burr sleeve 58 at the proximal end thereof 70. Arms 66 are joined by body portion 72 which portion includes location blade 74. The length of blade 74, ie., the location of distal edge 76, is at a fixed location relative to the reamer.

In use an assembly consisting of reamer 56, burr sleeve 58 and depth gauge 64 and a rotary power source (not shown)

are inserted into the pilot hole and oriented parallel to longitudinal axis 18 of femur 8. The assembly is then moved distally until distal edge 76 of blade 74 is in alignment with mark 24 on the surface of femur 8. Burr sleeve 58 is sized to remove sufficient bone from the medial cortex 53 of the greater trochanter 52 to allow for the neutral location of reamer 56, ie., to allow reamer 56 to be oriented co-axially with axis 18 of femur 8.The burr 58 is necessary if the medial cortex 53 overhangs the axis 18 of the femur and allows the surgeon to insert reamer at an angle (see FIG. 5) part way down the canal 54 and rotate the assembly laterally to the neutral position.

This location is sufficient to achieve stability of the distal reamer 56 so that it may be used as a guide for further instrumentation. In addition, the tip 57 of reamer 56 is positioned at the location of the distal tip of the hip implant chosen for implantation. At this point in the procedure the burr sleeve 58 and depth gauge 64 may be removed, leaving only reamer 56 in place.

Figure 8:
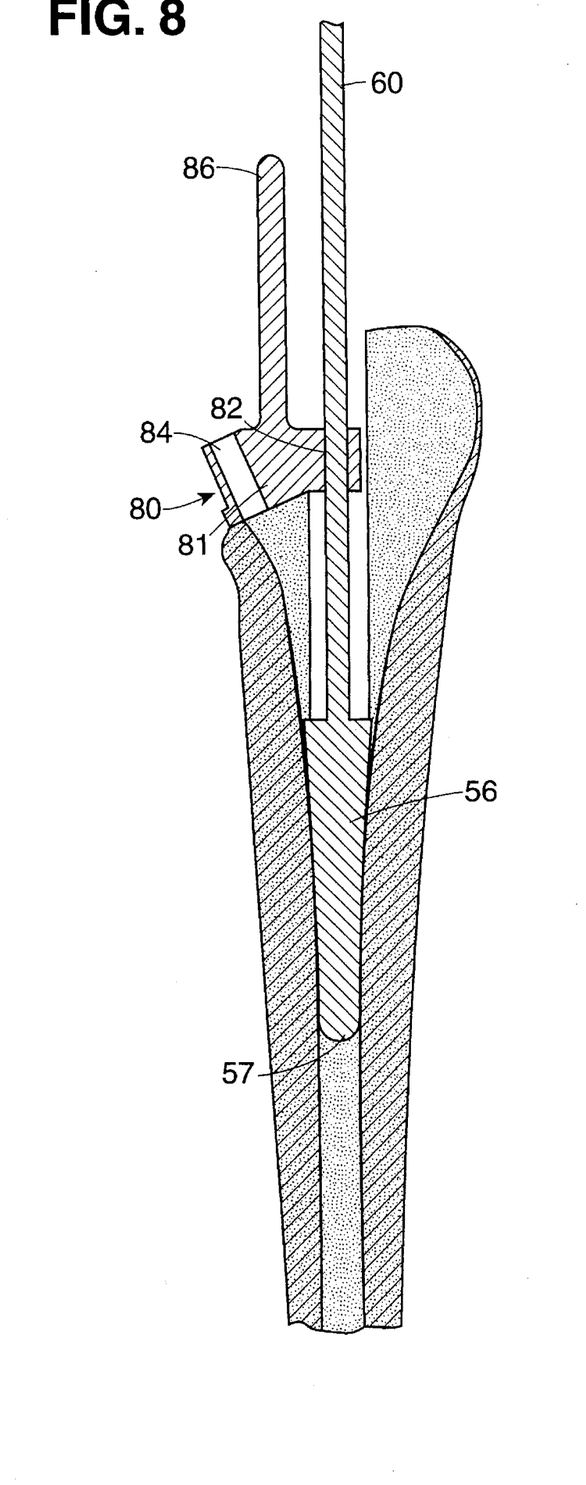
FIG. 8 is a cross-sectional view of the femur with the reamer in place with the burr removed and the metaphyseal template of the present invention mounted thereon.
Figure 9:
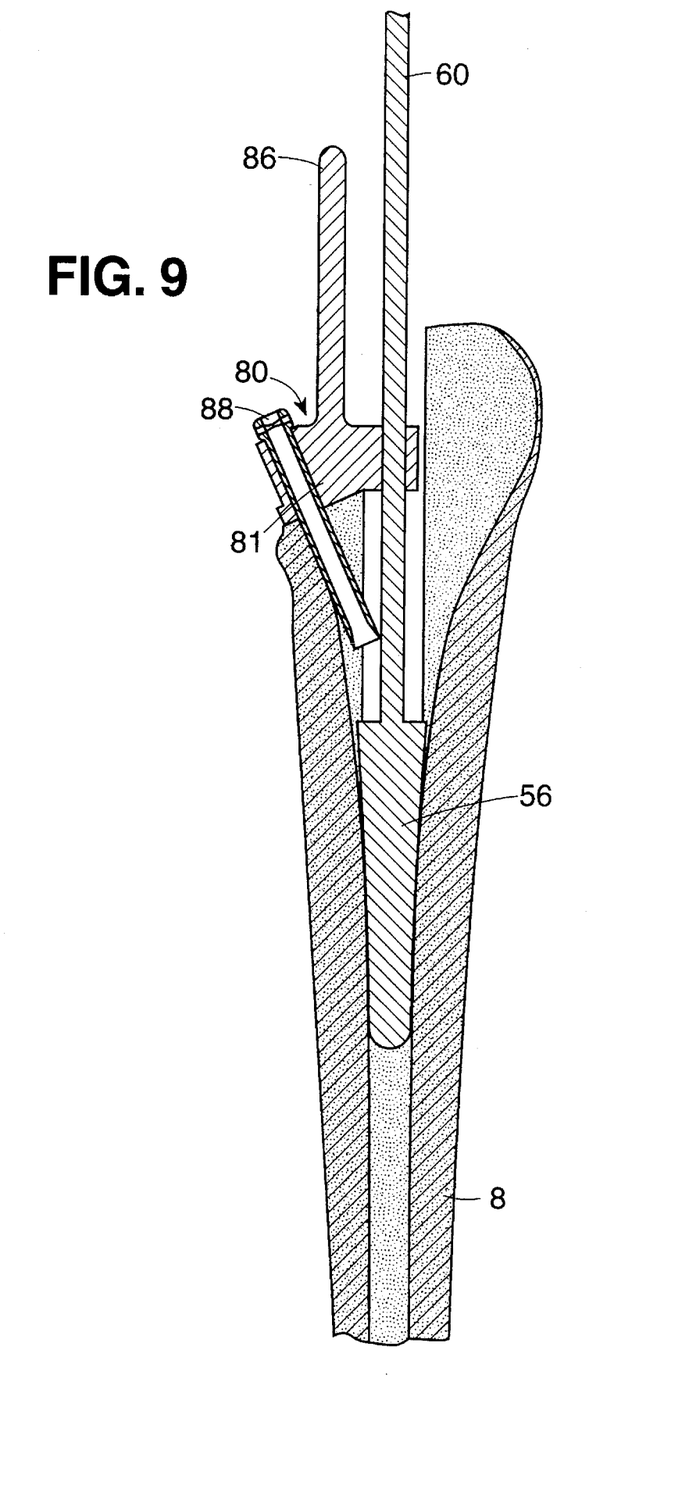
FIG. 9 is a cross-sectional view of the reamer/template shown in FIG. 8 further including an anchoring element.
Figure 10:
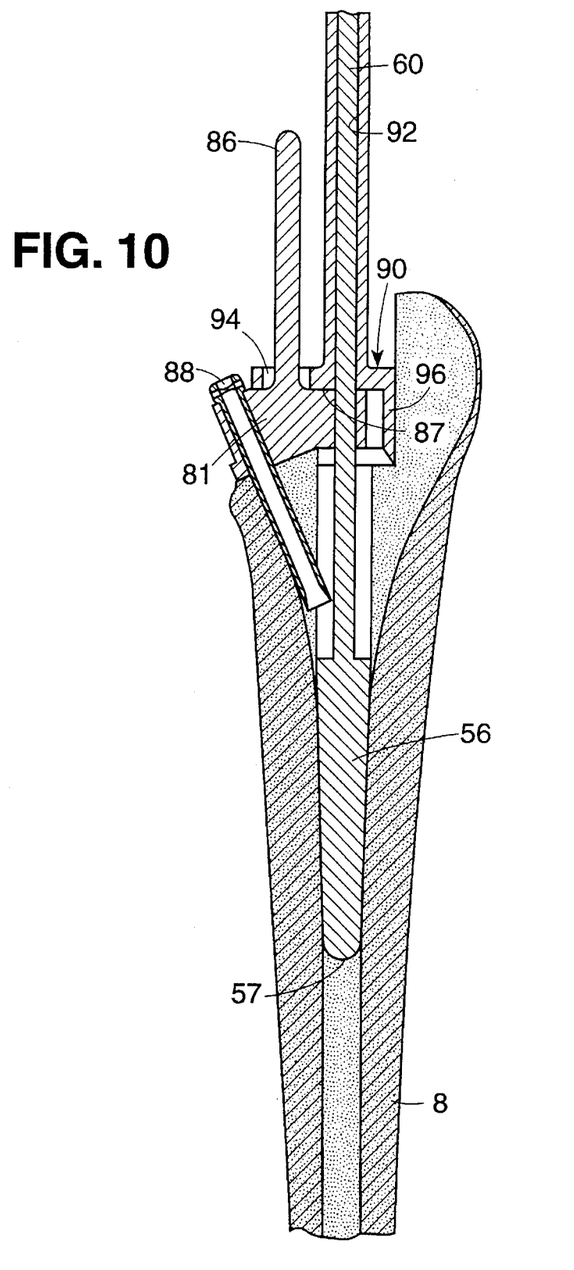
FIG. 10 is a cross-sectional view showing the chisel of the present invention mounted on the reamer and metaphyseal template.

Referring to FIGS. 8 through 10 there is shown reamer 56 now positioned to receive additional instrumentation. In this regard, there is shown a metaphyseal template generally denoted as 80 positioned on shaft 60. Template 80 has a body 81 which has a bore 82 sized to slidably receive shaft 60 of reamer 56. In addition, template 80 has a bore 84 adapted to receive an anchor element 88. In addition, a chisel alignment element 86, whose function will be described hereinafter, extends proximally from body 81.

Figure 8A:
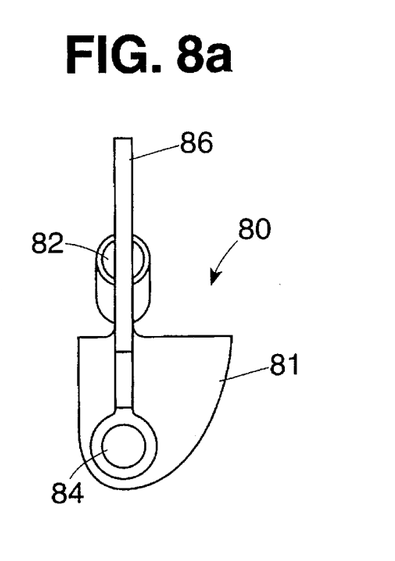
FIG. 8a is a top view of the metaphyseal template shown in FIG. 8.

As best seen in FIG. 8a, the perimeter of the template 80 mimics the proximal medial aspect of the chosen hip prosthesis at the osteotomy level. The template 80 is slid down shaft 60 and is able to rotate into the proper position on the osteotomy with respect to anteversion/retroversion. This location is determined by the surgeon and is the location in which the template 80 best corresponds to the shape of the opening produced by the osteotomy cut. Once the proper anteversion/retroversion is established, then anchor 88 is inserted through bore 84 into the metaphysis thereby locking the anteversion/retroversion position of template 80. In the preferred embodiment, anchor 88 is hollow to thereby remove cancellous bone upon its removal.

Figure 10A:
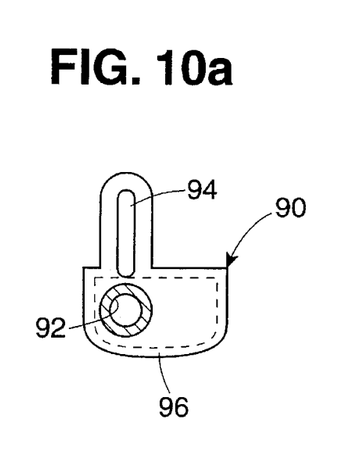
FIG. 10a is a top view of the chisel shown in FIG. 10.

Referring to FIGS. 10 and 10a there is shown chisel 90 which mounts on shaft 60 via a tubular portion 92. Chisel 90 includes a slot 94 which receives alignment element 86, in the form of a blade, locking the chisel in position, ie. preventing its rotation. Chisel 90 includes a partially circumferentially extending chisel blade 96 shaped to mimic the proximal lateral aspect of the implant. In this lateral position chisel blade 96 resects bone in a manner to expand the opening to the canal in the lateral aspect. This includes removal of part of the anterior and posterior sides of the opening. Not shown is an impaction head at the proximal end of tube 92 which allows the surgeon to impact the chisel to resect the medial cortex 53 of the greater trochanter 52. The depth of the cut made by chisel 90 is controlled by its contact with surface 87 of template 80.

Figure 11:
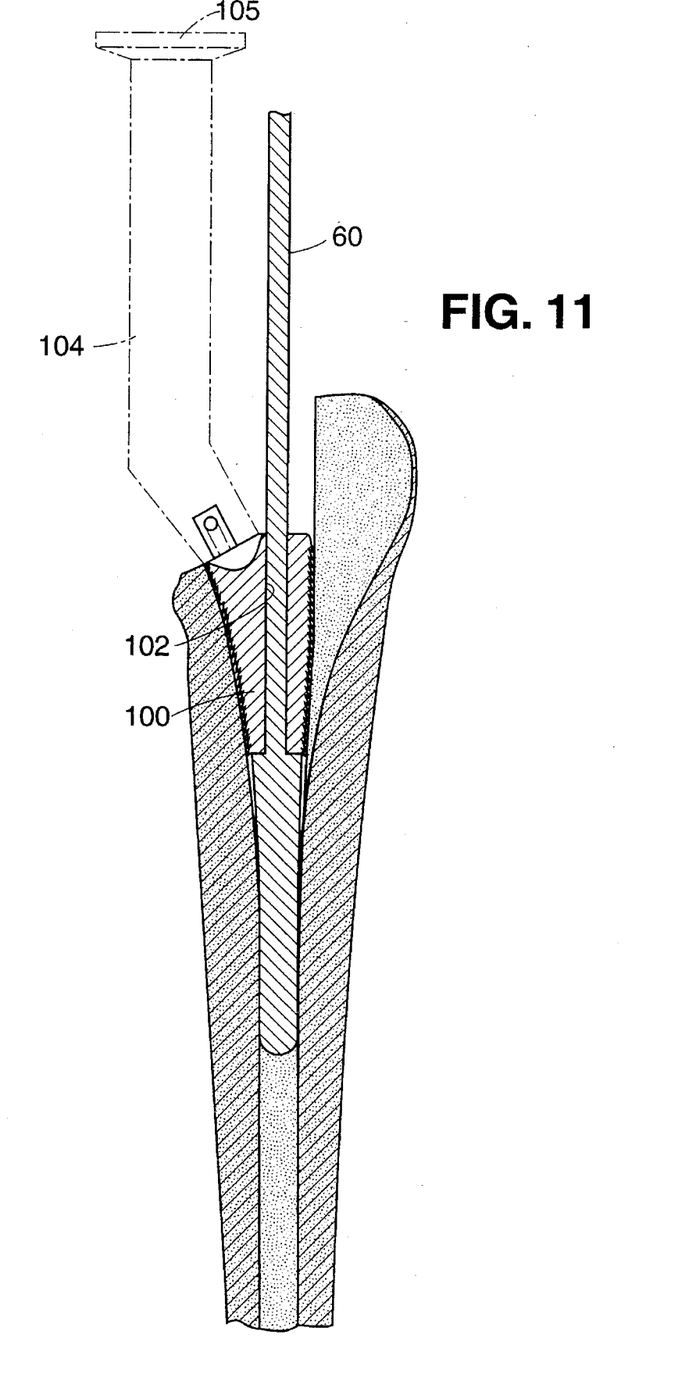
FIG. 11 is a cross-sectional view of the proximal broach of the present invention mounted on the reamer with a handle shown in phantom.

After the chisel 90 has been used, it is removed along with anchor 88 and template 80 and, as seen in FIG. 11, a proximal rasp or broach 100 is placed on shaft 60 and slid into position to shape the proximal femur. Rasp 100 has a bore 102 sized to slidably receive rod 60 and a removable handle 104 which is used to drive rasp 100 downwardly along rod 60 via impaction on head 105. By this process a substantial amount of cancellous bone is removed from the metaphysis. As with the distal reamer 56, the rasp 100 is shaped to mimic the proximal portion of the hip prosthesis to be implanted, except in the lateral side which will be formed by the final broach as will be discussed below. In the preferred embodiment the rasp or broach 100 is somewhat undersized so that the final broach forms the final cavity shape.

Figure 12:
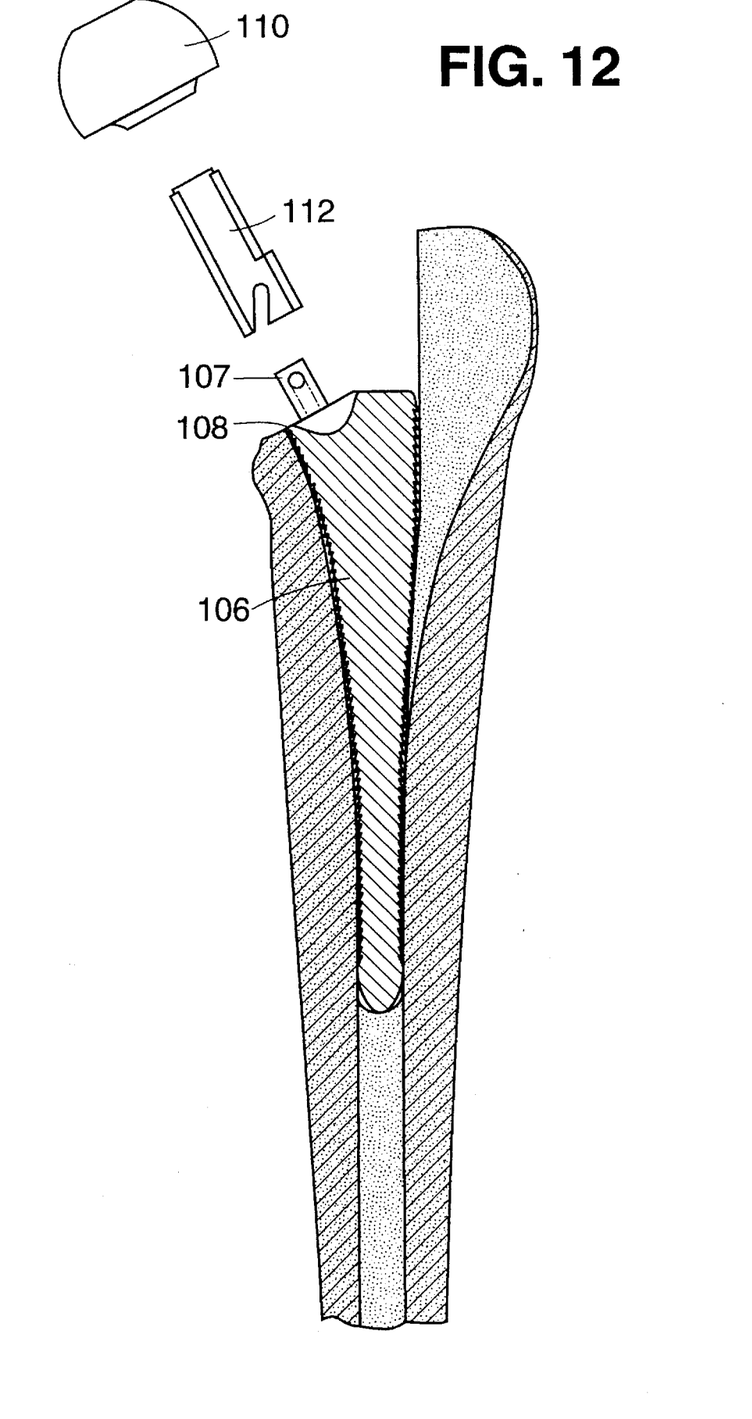
FIG. 12 is a cross-sectional view of the full sized broach of the present invention in the femur with modular head/neck elements shown in an exploded view.

Referring to FIG. 12 there is shown the final instrument to be used in the preparation of the cavity once reamer 56 and rasp or broach 100 are removed. Handle 104 is removed from rasp 100 and coupled to full rasp or broach 106 which has a shape which completely conforms to the shape of the hip stem to be implanted. Handle 104 is placed on trunion 107 and is again used to impact the rasp 106 to the final implant position. This is achieved when the proximal medial edge 108 of rasp 106 is at the same level as the medial surface of the osteotomy. Preferably this step removes only a small amount of bone in that the prior steps have already removed the bulk of bone to be resected.

Once rasp 106 is properly positioned, a trial head 110 and trial neck 112 are placed on trunion 107 and are used to ascertain the proper leg length and tissue balance. A variety of different size trial heads and at least one neck are provided for this purpose.

Once the correct head and implant combination are determined, the rasp 106 is removed. The selected hip stem prosthesis is then introduced.

Of course, one skilled in the art will understand that a kit of each of the above described instruments will be provided for each size implant stem (sometimes seven to eleven sets) with the exception of osteotomy height gauge 10, trochanteric burr sleeve 58 and reamer depth gauge which may be interchangeable among the various size sets. Other instruments may be included in the set.

While the entire instrument system has been disclosed and preferably should be used in its entirety, it is possible to use only one or two of the instruments during a cavity preparation.

While several examples of the present invention have been described, it is obvious that many changes and modifications may be made thereunto, without departing from the spirit and scope of the invention.

We claim:

1. A method for preparing the medullary canal of a femur to receive a prosthetic femoral implant having proximal and distal stem portions, comprising the steps:

providing a template, a gauge, a reamer, a metaphyseal template, a chise and a broach;

placing the template generally corresponding to the prosthetic hip implant on an x-ray of the femur to determine the level of an osteotomy cut with respect to the sulcus of the femur;

marking said determined position on the femur using the gauge locating off the sulcus;

performing the osteotomy by resecting the femur;

reaming the distal medullary canal to a predetermined depth with the reamer having an elongated shaft and a shape mimicking the shape of the distal stem portion of the prosthetic femoral implant;

placing the metaphyseal template on said elongated shaft to determine a proper anteversion/retroversion orientation thereof;

locking said metaphyseal template in place upon determining said proper anteversion/retroversion orientation;

placing the chisel having a shape generally corresponding to a lateral portion of the femoral implant at a proper alignment on said metaphyseal template and removing bone at the osteotomy level to form the proper lateral opening in said canal;

removing said template and said chisel: and placing the proximal broach over said elongated shaft of said reamer and shaping the proximal portion of said cavity with a broach having a shape generally conforming to the proximal portion of said implant.

2. A method as set forth in claim 1 further including the steps of removing said reamer and said proximal broach and thereafter broaching the entire cavity with a second broach having a shape corresponding to the actual femoral component implant.

3. The method as set forth in claim 2 further including the step of placing a series of trial heads in sequence on a trunion extending proximally from said second broach to determine the correct head size for said femoral implant.

4. A set of instruments for preparing the femoral canal of a femur for receiving a femoral component having a proximal and distal stem portion comprising:

a reamer having a shape corresponding to the distal stem portion and having an elongated drive shaft extending proximally therefrom;

a template having a bore therein for slidably receiving said elongated drive shaft and being rotatable thereon, said template having an alignment element thereon;

a chisel having a bore for slidably receiving said elongated drive shaft and having an alignment element thereon for engaging said alignment element on said template, said chisel for partially forming a lateral side of said femoral canal; and a first broach having a bore therein for receiving said elongated shaft for forming a proximal portion of said femoral canal while mounted on said shaft.

5. The set of instruments as set forth in claim 4 further including a gauge having an anteriorly-posteriorly extending arm for placement on the femur sulcus and having a distally extending shaft coupled to said arm with a platform slidably mounted on said shaft for transferring an osteotomy location from an x-ray template to said femur.

6. The set of instruments as set forth in claim 4 further including a second broach having a bore therein for receiving said elongated shaft and having a shape corresponding to the shape of the femoral component.

7. The set of instruments as set forth in claim 4 further including a depth gauge operatively coupled to said elongated drive shaft to set the location of the reamer within the femoral canal.

8. The set of instruments as set forth in claim 4 further including a cylindrical burr having a central bore for slidably receiving said elongated shaft of said reamer.

9. The set of instruments as set forth in claim 8 wherein said reamer includes means for rotating said burr upon the rotation of said reamer.

10. A kit of instruments for preparing the medullary canal of the femur to receive a hip prosthesis femoral component comprising:

a distal reamer having an elongated shaft extending proximally from a distal portion, said distal portion having a shape generally corresponding to the shape of a distal portion of said femoral component;

a metaphyseal template having a body including a first bore for slidably receiving said elongated shaft of said reamer and a second bore for receiving an anchor element, said template having a proximally extending alignment element; and a chisel having a body with a bore therein for slidably receiving said elongated shaft of said reamer and an aperture for receiving said proximally extending alignment element of said template.

11. The kit as set forth in claim 10 wherein said alignment element on said template is in the form of a blade and the aperture on said chisel is in the form of an elongated slot for receiving the blade on said template.

12. The kit as set forth in claim 10 further including a burr sleeve having a bore therein for receiving said elongated shaft of said distal reamer.

13. The kit as set forth in claim 12 further including a proximal broach including a bore for receiving said elongated shaft of said distal reamer, said proximal broach having a shape conforming to the shape of a proximal portion of said femoral component.

14. The kit as set forth in claim 13 further including a full broach having an outer envelope conforming to an outer envelope of said femoral component.

15. The kit as set forth in claim 14 further including a depth guide having means for mounting said guide on said elongated shaft of said distal reamer and having a proximally-distally extending location blade.

16. A femoral neck resetlion and reaming depth guide for using the sulcus of the femur as a guide surface and exclusive support surface comprising:

an elongated guide shaft having a calibrated scale along the length thereof;

an arm integral with said guide shaft and extending transversely from said guide shaft for engaging the sulcus of the femur and positioning said guide shall in a fixed position externally to the femur with said shall extending in a direction generally parallel to the longitudinal axis of the femur;

a marking platform slidably mounted on said guide shaft and having a looking element for locking the platform on said guide shaft with respect to the calibrations thereon; and where said arm integral with said guide shaft rests on said sulcus to provide the sole support of said femoral neck resection and reaming depth guide.

17. The femoral resection guide as set forth in claim 16 wherein the marking platform has a marking surface for guiding a marking device along the outer surface of the femur.

18. A reaming device for forming the medullary canal and the trochanteric region of the femur for receiving a prosthetic hip stem comprising:

a distal reamer having a shape corresponding to the distal portion of the hip stem;

an elongated drive shaft coupled to a proximal end of said distal reamer and extending in a proximal direction therefrom;

a burr sleeve having a bore for receiving said drive shaft; and an interengagable drive element on said burr and said distal reamer for driving said burr sleeve in unison with said distal reamer upon rotation of said drive shaft.

19. The reaming device as set forth in claim 18 wherein said distal reamer and said burr have helically fluted cutting elements.

20. The reaming device as set forth in claim 18 wherein the interengagable drive element comprise a polygonal shape drive shaft and a complimentary polygonal shaped bore in said burr.

21. The reaming device as set forth in claim 18 further comprising:
   a template having a bore thereon, said template having a alignment element thereon;
   a chisel having an alignment element thereon for engaging said alignment element on said template, said chisel for partially forming a lateral side of said femoral canal; and
   a broach having a bore therein for receiving said elongated drive shaft for forming a proximal portion of said femoral canal while mounted on said elongated drive shaft.

22. A set of instruments for preparing the proximal femoral canal of a resected femur for receiving a femoral component having a proximal and distal stem portion comprising:
   a reamer having a shape corresponding to the distal stem portion and having an elongated shaft extending proximally therefrom;
   a template having a bore therein for slidably receiving said elongated drive shaft and being rotatable thereon, said template having an alignment element thereon;
   a chisel having a bore for slidably receiving said elongated drive shall and having an alignment element thereon for engaging said alignment element on said template, said chisel for partially forming a lateral side of said proximal femoral canal;
   a first broach having a bore therein for receiving said elongated shaft for forming a proximal portion of said femoral canal while mounted on said shaft; and
   a second broach having a bore for receiving said elongated shaft.

23. The set of instruments as set forth in claim 22 further including a depth gauge operatively coupled to said elongated shaft to set the location of said guide element within the femoral canal.

* * * * *